Figure 1:
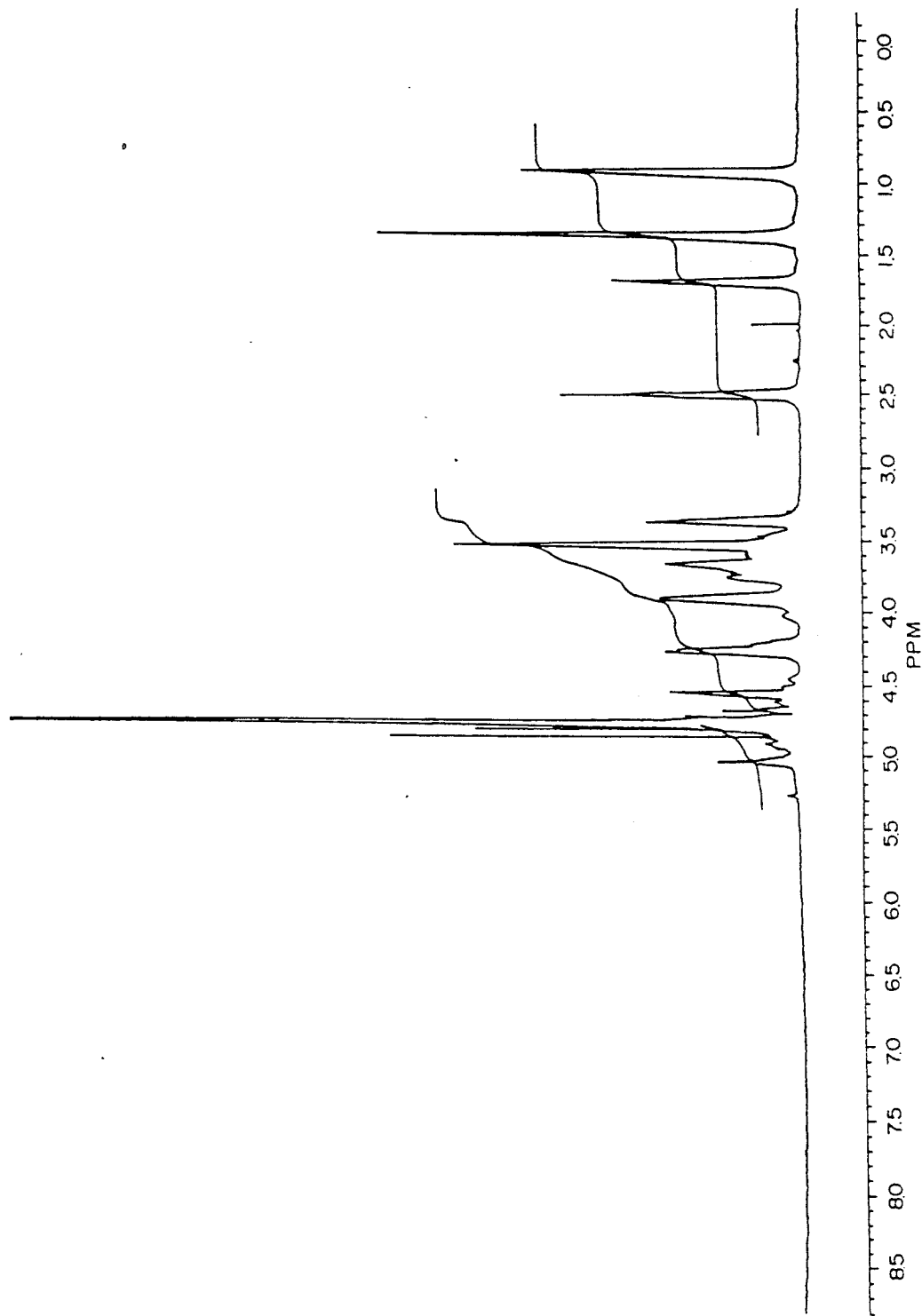

United States Patent [19]

Morishita et al.

[11] Patent Number: 5,132,112

[45] Date of Patent: Jul. 21, 1992

[54] HS-142-1 COMPOUNDS

[75] Inventors: Yoshikazu Morishita, Kanagawa; Mitsuru Takahashi, Tokyo; Koji Yamada, Shizuoka; Tomoyuki Sano, Tokyo; Isao Kawamoto, Kanagawa; Katsuhiko Ando, Tokyo; Hiroshi Sano, Tokyo; Yutaka Saito, Tokyo; Hiroshi Kase, Tokyo; Yuzuru Matsuda, Tokyo, all of Japan

[73] Assignee: Kyowa Hakko Kogyo Kabushiki Kaisha, Tokyo, Japan

[21] Appl. No.: 682,349

[22] Filed: Apr. 9, 1991

[30] Foreign Application Priority Data

Apr. 10, 1990 [JP] Japan ................................. 2-94295

[51] Int. Cl.$^5$ ........................ A61K 35/70; C12D 1/02
[52] U.S. Cl. ..................................... 424/118; 435/171
[58] Field of Search ........................ 424/118; 435/171

[56] References Cited

FOREIGN PATENT DOCUMENTS 0266170  5/1988  European Pat. Off. .
WO8900428  1/1989  PCT Int'l Appl. .

OTHER PUBLICATIONS

Annual Review of Pharmacological Toxology (1989).
Heparin Article, vol. 9, No. 6, Jun. 1987.

*Primary Examiner*—Jerome D. Goldberg
*Attorney, Agent, or Firm*—Schweitzer, Cornman & Gross

[57] ABSTRACT

Compounds comprising a linear $\beta 1 \rightarrow 6$ glucan esterified by caproic acid, the number of D-glucose residues being from 7 to 40 and the number of caproic acid residues being from 2 to 30, may be be obtained by fermentation of a microorganism of the genus *Aureobasidium*. These compounds are designated HS-142-1. Preferred microorganism is *Aureobasidium pullulans* var. *melanigenum* KAC-2383 (FERM-BP 2407).

The compounds of the present invention exhibit excellent antagonistic activity to ANP and are capable of inhibiting the bonding of ANP to ANP receptors.

6 Claims, 3 Drawing Sheets

HS-142-1 COMPOUNDS

The present invention relates to compounds designated HS-142-1 and processes for their preparation by fermentation of a microorganism.

The compounds of the present invention are antagonistic to the receptors of atrial sodium peptide (hereinafter referred to as ANP), which participates in certain diseases such as, for example, essential hypertension and congestive heart failure.

Compounds having such an activity may be used, for example, for treating hypotension and polyuria. In particular, with regard to polyuria which may occurs at an earlier stage of diabetes, it was previously known that compounds antagonistic to the ANP receptors may effectively be used for treating such diseases [WO 89/00428]. Also compounds of this type may be used for the study of the pathological role of ANP in essential hypertension, congestive heart failure and the like.

ANP is a peptide hormone secreted mainly from the atrium and exhibits strongly sodium-diuretic activity and blood pressure-reducing activity. Also it has been reported that ANP is capable of adjusting the volume of extracellular body liquid indirectly through the action of the ANP receptors distributed in various organs. However, the function and physiological role of ANP has, in summary, not yet been sufficiently clarified, and in consequence, the provision of compounds which are specifically antagonistic to ANP receptors has eagerly been desired [Annu. Rev. Pharm. Tox. 29, 23–54 (1989)].

With regard to compounds which are specifically antagonistic to ANP receptors, it has been disclosed that some ANP derivatives may be antagonistic to vaso-relaxation induced by ANP (JP-A-225399/88). But any other substances having antagonistic activity to other ANP receptors have not yet been reported.

There are methods known for investigating the physiological and pathological activities of ANP by blocking the action of ANP [Proc. Natl. Acad. Sci. 85, 3155–3199 (1988)] and by using heparin which forms an ionic bond with ANP [Hypertension, 9, 607–610 (1987)]. However, these methods are likely to be inadequate for completely investigating the actual action of ANP under physiological conditions because the antibodies and heparin used in these methods are incapable of bonding directly to ANP receptors.

Thus, for example, for the purpose of curing certain diseases such as hypotension and polyuria and investigating the physiological and pathogenic role of ANP, it has been desired to provide a substance capable of bonding to the ANP receptors and thereby to blocking the action of ANP.

We have found that compounds capable of inhibiting the bonding of ANP to the receptor may be obtained by fermentation of a microorganism belonging to the genus Aureobasidium. These compounds have been isolated and purified to investigate their physico-chemical characteristics. As a result, we have confirmed that the resultant compounds (hereinafter collectively referred to as HS-142-1) are novel.

The present invention is directed to provide new physiologically active compounds which exhibit significantly high antagonistic activity to the ANP receptors and processes for their preparation.

The present invention provides new physiologically active compounds comprising a linear $\beta 1 \rightarrow 6$ glucan esterified with caproic acid, the number of D-glucose residues being from 7 to 40 and the number of caproic acid residues being from 2 to 30.

The compounds of the present invention are exemplified by the compounds HS-142-1a, HS-142-1b and HS-142-1c as follows:

| Compounds | D-glucose residues | Caproic acid residues |
|---|---|---|
| HS-142-1a | 28 | 11 |
| HS-142-1b | 17 | 11 |
| HS-142-1c | 13 | 6 |

These compounds form further embodiments of this invention.

The physico-chemical characteristics of HS-142-1a, HS-142-1b and HS-142-1c are as follows:

HS-142-1a

① Nature: White powder.
② Melting point: 175°–185° C.
③ Molecular formula: $C_{234}H_{392}O_{152}$.
④ Mass spectrum (negative mode FAB mass spectrum): Found: M/Z 5536.5 (M-H)$^-$. Calculated: M/Z 5637.3.
⑤ Specific rotation: $[\alpha]^{24}_D = -29.4°$ (c 0.24, aqueous solution).
⑥ Infrared absorption spectrum (KBr tablet method): cm$^{-1}$: 3420, 2930, 1730, 1635, 1455, 1380, 1250, 1170, 1045.
⑦ Ultraviolet absorption spectrum (aqueous solution): Only terminal absorption visible.
⑧ $^1$H-NMR spectrum (500 MHz, in D$_2$O): As shown in FIG. 1 herein.
⑨ Colour reaction: Positive in the reactions with anisaldehyde, sulfuric acid and iodine. Negative in the reactions with ninhydrin, dinitrophenylhydrazine, ferric chloride, bromocresol green and Dragendorff's reagent.

HS-142-1b

Figure 2:
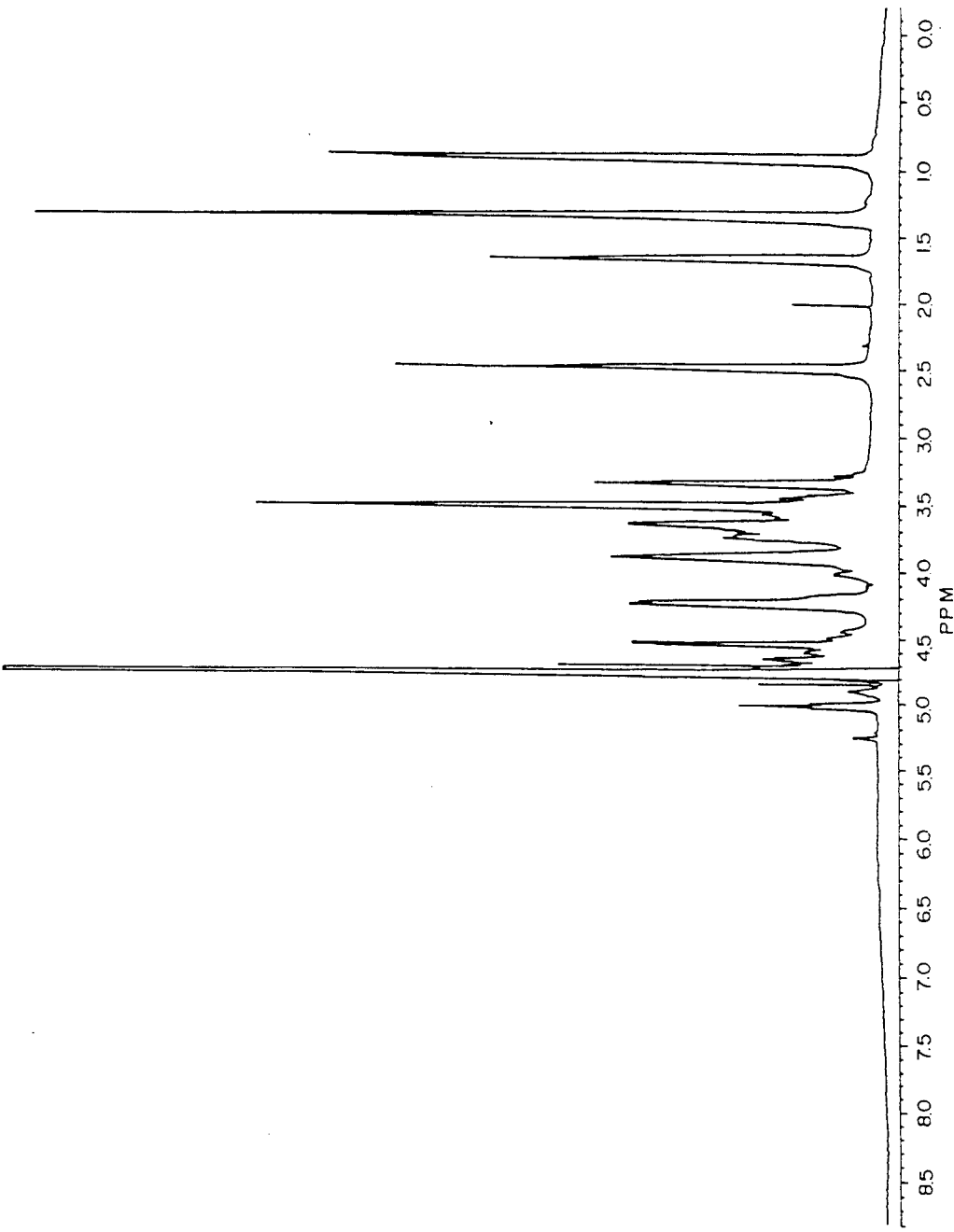

① Nature: White powder.
② Melting point: 175°–185° C.
③ Molecular formula: $C_{150}H_{252}O_{94}$.
④ Mass spectrum (negative mode FAB mass spectrum): Found: M/Z 3557.9 (M-H)$^-$. Calculated: M/Z 3558.5.
⑤ Specific rotation: $[\alpha]^{24}_D = -21.1°$ (c 0.06, aqueous solution).
⑥ Infrared absorption spectrum (KBr tablet method): cm$^{-1}$: 3425, 2925, 1730, 1645, 1455, 1375, 1250, 1170, 1050.
⑦ Ultraviolet absorption spectrum (aqueous solution): Only terminal absorption visible.
⑧ $^1$H-NMR spectrum (500 MHz, in D$_2$O): As shown in FIG. 2 herein.
⑨ Colour reaction: Positive in the reactions with anisaldehyde, sulfuric acid and iodine. Negative in the reactions with ninhydrin, dinitrophenylhydrazine, ferric chloride, bromocresol green and Dragendorff's reagent.

HS-142-1c

① Nature: White powder.
② Melting point: 175°–185° C.
③ Molecular formula: $C_{114}H_{192}O_{72}$.

④ Mass spectrum (negative mode FAB mass spectrum): Found: M/Z 2713.3 (M-H)⁻. Calculated: M/Z 2734.1.

⑤ Specific rotation: $[\alpha]^{24}_D = -26.2°$ (c 0.4, aqueous solution).

⑥ Infrared absorption spectrum (KBr tablet method): cm⁻¹: 3400, 2935, 1735, 1650, 1460, 1380, 1255, 1165, 1050.

⑦ Ultraviolet absorption spectrum (aqueous solution): Only terminal absorption visible.

Figure 3:
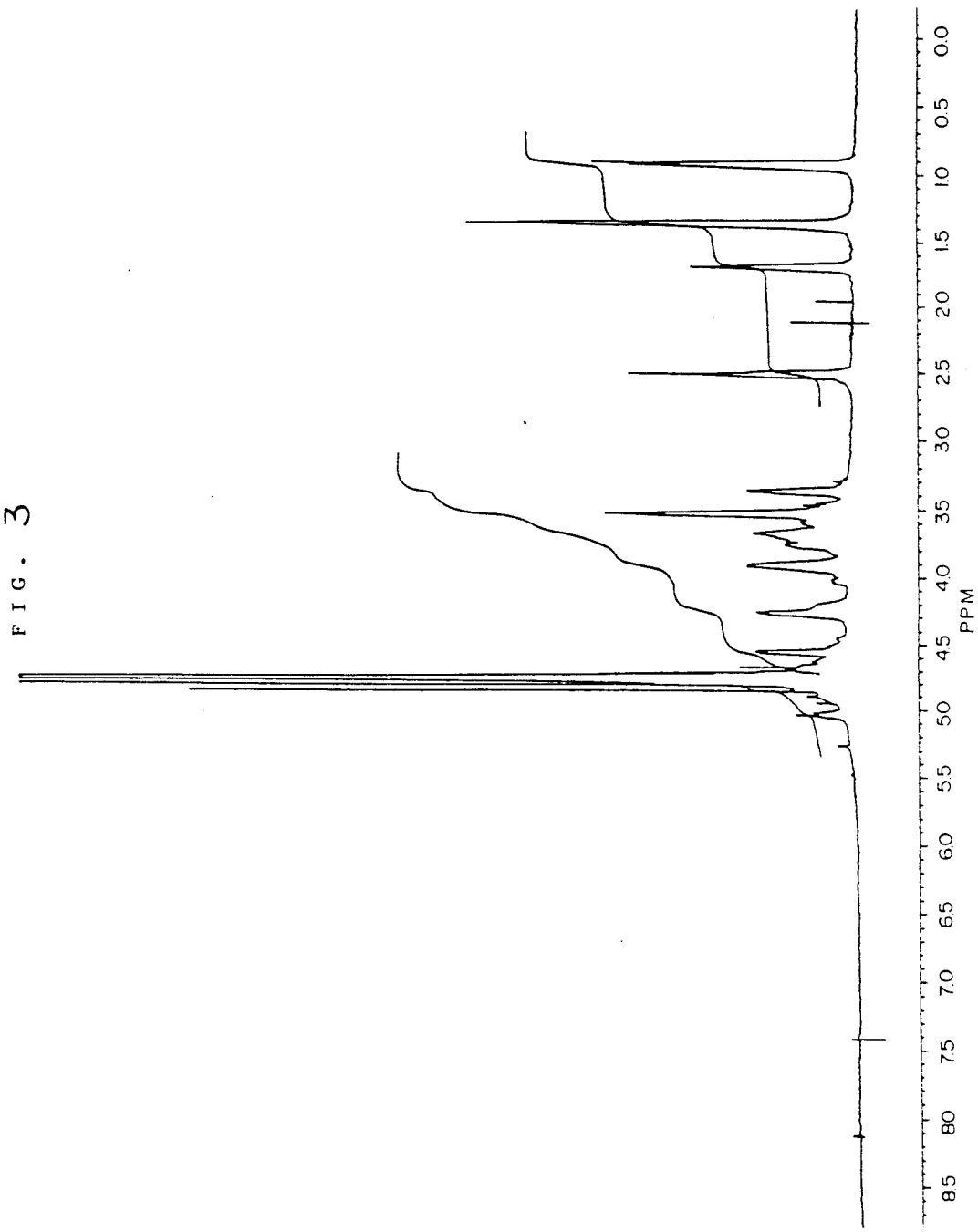

⑧ ¹H-NMR spectrum (500 MHz, in $D_2O$): As shown in FIG. 3 herein.

⑨ Colour reaction: Positive in the reactions with anisaldehyde, sulfuric acid and iodine. Negative in the reactions with ninhydrin, dinitrophenylhydrazine, ferric chloride, bromocresol green and Dragendorff's reagent.

The following instruments were used to measure the data as set forth:

Melting point: Micro melting point measuring device (Yanagimoto Seisakusho, Japan).

Specific rotation: DIP-370 Digital polarometer (Nihon Bunko K.K., Japan).

IR absorption spectrum: JIR-RFX 30 FTIR spectrophotometer (Nihon Denshi K.K., Japan).

UV absorption spectrum: 200-20 type Double beam spectrophotometer (Hitachi Ltd., Japan).

Mass spectrum: JMS-SX 102 Mass spectrometer (Nihon Denshi K.K., Japan).

¹H-NMR spectrum: AM-500 NMR device (Bruker, U.S.A.)

Mass spectra were calculated by the most abundant MS method.

According to another embodiment of this invention, HS-142-1 may be prepared by culturing a microorganism belonging to the genus Aureobasidium capable of producing HS-142-1 in a suitable culture medium to accumulate HS-142-1 in the cultured broth and recovering HS-142-1 therefrom.

Although it is possible, if desired, to use for the process of the present invention any and all microorganism of the genus Aureobasidium so far as they are capable of producing the compounds HS-142-1 by fermentation, the microorganism used in the example described hereinafter is *Aureobasidium pullulans* var. melanigenum KAC-2383, which we have isolated from the fallen leaves of Japanese red pine (*Pinus densiflora*) collected in Yamaguchi-ken, Japan.

The mycological characteristics of this strain are as follows:

In the case where this strain is cultured at a temperature of 20° C. using malt-extract agar medium, the diameter of the resultant colonies reaches, for example, 36–40mm 18 days after the beginning of the culturing. The colonies are coloured in yellowish brown to dark blackish brown. The optimal growth temperature is from 20° to 30° C. (preferably from 25° to 27° C.). The growth pH is from 2 to 8 (preferably from 3 to 5). The hyphae have partitions and are branched. The hyphae are smooth and at early stage colourless, and then some of them become dark brown. The width of the hyphae is from 2 to 10 μm. The conidium-forming cells are not differentiated. The conidia are formed, so to speak, simultaneously and directly from the hyphae. Ontogenesis of conidia is the budding-type. The conidia formed from the hyphae grow further and form yeast-like buddings. The conidia are smooth and oval and of the mono-cell type.

Although the size of the conidia is variable, they usually have a length of 6.5-15.5 μm and a width of 2.5-4 μm. Even though the above-mentioned anamorph may be observed, no telemorph is found.

With reference to the mycological characteristics as set forth, this microorganism was identified as *Aureobasidium pullulans* (de Bary) Arnaud var. melanigenum Hermandies-Nijhof and named by us as *Aureobasidium pullulans* var. melanigenum KAC-2383. The present strain was deposited with the Fermentation Research Institute (FRI). located at 1-3, Higashi 1-chome, Tsukuba-shi, Ibaraki-ken, Japan on 1 May 1989 on the basis of The Treaty of Budapest, the deposition number being FERM-BP 2047. This strain forms a further embodiment of the present invention.

The mycological characteristics of *Aureobasidium pullulans* var. melanigenum are described in detail in "Aureobasidium and allied genera" written by E. J. Hermanides-Nijhof and indicated in Studies in Mycology, (Baarn), Vol. 15, pages 141-177 (1977).

The microorganisms which may be used for the process of the present invention may be cultured in a conventional manner applicable to fungi. Thus, both the organic and synthetic media may be used so far as they contain appropriately various assimilable sources of carbon, nitrogen and inorganic substances.

Preferred carbon sources for this process are exemplified by carbohydrates such as glucose, fructose, sucrose, lactose, stabilose, starch, dextrin, mannose, maltose, molasses and mushed potato extract; organic acids such as citric acid, malic acid, acetic acid and fumaric acid; alcohols such as methanol and ethanol; hydrocarbons such as methane, ethane and n-paraffin; amino acids such as glutamic acid; glycerol and cotton seed oil.

Preferred nitrogen sources for this process are exemplified by ammonium salts such as ammonium chloride, ammonium sulfate and ammonium phosphate; amino acids such as aspartic acid. glutamin, cystin and alanine; urea, malt extract, peptone, meat extract, yeast extract, dried yeast, corn steep liquor, soyabean powder, cotton seed cake, soyabean casein, cazamino acid, Pharmamedia, soluble vegetable protein, vegetable juice and fruit juice.

Preferred inorganic substances for this process are exemplified by potassium hydrogen phosphate, potassium dihydrogen phosphate, sodium dihydrogen phosphate, magnesium sulfate, ferrous sulfate, manganese sulfate, cobalt sulfate, zinc sulfate, calcium pantothenate, ammonium molybdate, aluminum potassium sulfate, barium carbonate, calcium carbonate, cobalt chloride and sodium chloride.

If desired, it is possible to add to the medium various substances (e.g. vitamins) capable of promoting the growth of the microorganism or the productivity of HS-142-1.

In the case where the microorganism used requires special substances for the growth, it is necessary to use such substances, Usually, culturing may be effected with shaking with or without aeration at a temperature of from 15 to 25° C. and around a neutral pH. After completion of culturing for 3 to 6 days, the accumulated amount of HS-142-1 reaches a maximum.

HS-142-1 accumulated in the cultured broth may be isolated and purified in a conventional manner e.g. by techniques known for the isolation and purification of substances obtained by fermentation.

Preferred methods for isolation and purification of HS-142-1 are exemplified by extraction of cell debris by the use of suitable solvents such as, for example, acetone and methanol; removal of cell debris by filtration and centrifugation; partition using suitable solvents; adsorption and elution of the active substances on chromatographic columns containing adsorbing resins such as silica gel, alumina, cellulose, diatomaceous earth, magnesium silicate; gel filtration chromatography using appropriate media; and thin layer chromatography.

In one preferred embodiment, HS-142-1 may be isolated from the cultured broth and purified in the following manner:

Cells are removed from the cultured broth by filtration or centrifugation. The resultant filtrate or supernatant is passed through a column packed with a suitable adsorbing resin such as, for example, Diaion HP-20 (commercial product of Mitsubishi Kasei K.K., Japan) to adsorb the active substances onto the resin.

A suitable solvent such as, for example, methanol is needed to elute the active substances. The eluate is concentrated under reduced pressure. Through successive repeating silica gel chromatography, crude powders of HS-142-1 are obtained. The crude powders are dissolved in a small amount of 70% methanol and adsorbed onto Diaion HP20ss (commercial product of Mitsubishi Kasei K.K., Japan), washed with 70% methanol and eluted with 100% methanol. The eluate is concentrated to dryness under reduced pressure to obtain yellowish white powders.

Successive gel filtration chromatography of the resultant powders using Sephadex LH-20 (commercial product of Pharmacia Fine Chemicals AB, Sweden) and Bio-Gel P4 (commercial product of BioRad AB, Sweden) as the gel filtration media gives colorless powders of HS-142-1.

In this case, purification of HS-142-1 may be monitored by developing the intermediate purification product on a thin layer chromatographic plate which may be visualized by spraying 50% sulfuric acid and heating, or by detecting the terminal absorption of HS-142-1 by means of an appropriate detector.

According to a yet further embodiment of this invention, we provide a composition antagonistic to ANP receptors comprising HS-142-1 in admixture with a physiologically acceptable carrier, diluent or excipient. Also provided is use of HS-142-1 to prepare compositions antagonistic to ANP receptors.

The following non-limiting example and experiments illustrate the invention.

EXAMPLE 1

A medium (pH 6.0; 15 ml) composed of glucose (1.0 g/dl), peptone (0.5 g/dl; commercial product of Kyokuto Seiyaku K.K., Japan), dried yeast (0.5 g/dl, Ebios, commercial product of Asahi Bier K.K., Japan), V-8 vegetable juice (0.2 dl/dl, commercial product of Campbell Corpn., U.S.A.) and calcium carbonate (0.3 g/dl) was used to culture a seed of *Aureobasidium pullulans* var. melanigenum KAC-2383 at a temperature of 25° C. with shaking until the microorganism grew sufficiently.

The resultant seed culture (5 ml) was then cultured at a temperature of 25° C. for 2 days with shaking by using a medium (50 ml) having the same composition. The cultured broth (250 ml) was then transferred to a medium (2.5 l) and put in a jar fermenter (5 l) for culturing at a temperature of 25° C. for one day with aeration and shaking (2.5 l/min, 250 r.p.m.), the medium having the same composition as set forth.

The cultured broth (5 l) was transferred to a 200 l jar fermenter containing a production medium (100 l) having the following composition:

glucose (3 g/dl), starch (1 g/dl), Pharmamedia (1.5 g/dl), magnesium sulfate·$7H_2O$ (0.1 g/dl), sodium chloride (0.3 g/dl), potassium dihydrogen phosphate (0.1 g/dl), cobalt chloride·$6H_2O$ (6 µg/dl), ferrous sulfate·$7H_2O$ (10 mg/dl), copper sulfate·$5H_2O$ (70 mg/dl), zinc sulfate·$7H_2O$ (2 mg/dl), calcium carbonate (0.5 g/dl) [pH 7.0].

After completion of the fermentation at a temperature of 25° C. for 5 days with aeration and shaking (100 l/min. 350 r.p.m.), the cultured broth was centrifuged to remove the cells. The supernatant (100 l) was adsorbed onto a column packed with Diaion HP-20 (10 l, commercial product of Mitsubishi Kasei K.K., Japan), which was washed with 50% (v/v) methanol (30 l). The elution was effected with methanol (30 l). The methanol eluate was concentrated under reduced pressure to dryness to give brown powders (51.8 g).

The powders were applied to a silica gel column packed with Silica gel 60 (5 l, commercial product of Merck AG. Germany; 63 to 200 µm) equilibrated with chloroform/methanol (8:2 v/v) and eluted with chloroform/methanol (4:6 v/v) after washing with chloroform/methanol (15 l, 8:2 v/v). The eluate was concentrated under reduced pressure to dryness to give yellow powdes of semi-purified HS-142-1 (40.3 g).

The resultant semi-purified product (4 g) was applied to a silica gel column (400 ml) packed with Silica gel 60 (commercial product of Merck AG., Germany; 40 to 63 µm) and equilibrated with chloroform/methanol/water (7:3:0.5 v/v) and eluted with chloroform/methanol/water (1200 ml, 6:4:0.7 v/v) after washing with chloroform/methanol/water (1200 ml; 7:3:0.7 v/v). The eluate was divided into fractions (each 15 ml). HS-142-1 were mainly found in fraction Nos. 22-53, which were then combined and concentrated to dryness under reduced pressure.

The dried material was dissolved in a small amount of 50% (v/v) methanol and applied to a column ($\phi 28 \times 450$ mm) packed with HP-20ss 180 ml; commercial product of Mitsubishi Kasei K.K., Japan), equilibrated with 50% (v/v) methanol and eluted with methanol (600 ml) after successive washing with 50% (v/v) methanol (600 ml) and 70% (v/v) methanol (600 ml). Fractions containing HS-142-1 were collected, combined and concentrated to dryness to give HS-142-1 (413 mg).

The crude HS-142-1 was dissolved in methanol (3 ml) ans applied to a column packed with Sephadex LH-20 (1000 ml, commercial product o: Pharmacia Fine Chemicals AB. Sweden) equilibrated with methanol and eluted with methanol. Fractions were collected every 10 ml. Fraction Nos. 37-44 which contained HS-142-1 were collected, combined and concentrated to dryness to give colourless powders (304 mg). The powders (90 mg) were dissolved in water (2 ml) and applied on a column ($\phi 38 \times 450$ mm) packed with Bio-Gel P4 (200-400 mesh, commercial product of BioRad, Sweden) equilibrated wit water and eluted with water. Fractions were collected every 12 ml. Fraction Nos. 16-26 containing HS-142-1 were respectively freeze-dried to give colourless powders of HS-142-1 (67.9 mg). Among them, HS-142-1a, HS-142-1b and HS-142-1c were respectively found in fraction Nos. 18, 22 and 25.

The following experiments indicate the antagonistic activities of HS-142-1 to ANP receptors.

EXPERIMENT 1

Inhibition of binding of ANP to ANP receptor in rabbit kidney cortex:

(1) Method:

Inhibiting activity against the binding of ANP to ANP receptor in rabbit kidney cortex was measured in vitro using a method similar to the M. A. Napier et. al method [Proc. Natl. Acad. Sci., 81, 5946–5950 (1984)]. In this case, the fractions obtained by elution with Bio-Gel P4 as described in the example and crushed rabbit kidney cortex homogenate, were used.

(2) Results:

The binding of $(3\text{-}[^{125}I]$ iodotyrosyl$^{28})$ rat ANP to ANP receptor in rabbit kidney cortex was inhibited by separately applying HS-142-1a, HS-142-1b and HS-142-1c (each 1 µg/ml) which resulted in inhibition ratios of 68, 76 and 70% respectively. It was also noted that active compounds other than HS-142-1a, HS-142-1b and HS-142-1c exhibited a similar inhibiting activity.

EXPERIMENT 2

Antagonistic of ANP induced increase of cGMP level of LLC-PK1 cells:

(1) Method:

Antagonistic activity of HS-142-1 to the increase of cGMP level of LLC-PK1 cells induced by ANP (10 nM) was measured using a method similar to the F. Murad et al. method [J. Biol. Chem., 263, 3720–3728 (1988)].

(2) Results:

The increase of cGMP level of LLC-PK1 cells by the action of ANP (10 nM) was inhibited by applying separately HS-142-1a, HS-142-1b and HS-142-1c (each 10 µg/ml) to result in inhibition ratios of 60%, 61% and 41% respectively.

EXPERIMENT 3

Antagonism of ANP induced vasorelaxation in rabbit thoracic aorta.

(1) Method:

Thoracic aorta was collected from a Japanese white rabbit (male) to prepare a sample in the form of a spiral having a width of about 3 mm. The sample was suspended in a Magnus tube with a load of 2 g. The tube was filled with Krebs-Henseleit 1 solution composed of sodium chloride (118 mM), potassium chloride (4.75 mM), calcium chloride (2.54 mM), magnesium sulfate (1.19 mM), sodium bicarbonate (12.5 mM), potassium dihydrogen phosphate (1.19 mM) and glucose (10.0 mM) and was aerated with a mixed gas composed of 95% $O_2$ and 5% $CO_2$, while the inside of the tube was kept at a temperature of 37° C. The induced tension was measured on an equal scale by means of an isometric transducer and recorded with an ink-pen recorder.

After having been stabilized for a period of more than 60 minutes, a test drug was applied to the sample. The sample was constricted with addition of phenylephrine to measure the vasorelaxation reaction induced by adding ANP $(3 \times 10^{-9}\text{gM})$.

(2) Results:

The results are shown in Table 1, which indicates clearly the inhibiting activity of HS-142-1a against the vasorelaxation induced by ANP.

TABLE 1

| | Concentration of additive (µg/ml) | |
|---|---|---|
| | 1 | 3 |
| Inhibition ratio (%) | 45.7 | 61.0 |

EXPERIMENT 4

Antagonism of ANP-induced diuresis in the anesthetized rat:

(1) Method:

Male rats (Sprague-Dowley strain) were used as test animals. Each animal was anesthetized by intraperitioneal administration of pentabarbital. In order to collect urine, a canule was inserted into the urinary bladder which was exposed by incision of a part of abdominal skin. A canule was inserted into the femoral vein to administer the test compound and supply physiological saline.

Each animal was administered with physiological saline at a constant flow rate and was stabilized before the beginning of the test. Urine was collected from the animal for a given period of time to measure the urine volume. The animal was intravenously given a test compound or solvent, followed by intravenous administration of ANP. Then, urine was collected from the animal to measure the inhibiting effect of the test compound against the diuretic activity of ANP.

(2) HS-142-1a (1 mg/kg) inhibited the increase of the urine volume induced by the administration of ANP at an inhibition ratio of 93.0%.

With reference to the above-mentioned Experiments 1-4, it is apparent that the compounds HS-142-1 are capable of inhibiting the binding of ANP to its receptor and thus are antagonistic to the activity of ANP in vivo and in vitro.

We claim:

1. A HS-142-1 compound comprising a linear $\beta 1 \rightarrow 6$ glucan esterified by caproic acid, the number of D-glucose residues being 28 and the number of caproic acid residues being 11, having substantially the following physio-chemical characteristics:
    1) Nature: White powder
    2) Melting point: 175°–185° C.
    3) Molecular formula: $C_{234}H_{392}O_{152}$
    4) Mass spectrum (negative mode FAB mass spectrum): Found: M/Z 5536.5 (M-H)$^-$ Calculated: M/Z 5637.3
    5) Specific rotation: $[\alpha]^{24}{}_D = -29.4°$ (c 0.24, aqueous solution)
    6) Infrared absorption spectrum (KBr tablet method): cm$^{-1}$: 3420, 2930, 1730, 1635, 1455, 1380, 1250, 1170, 1045
    7) Ultraviolet absorption spectrum (aqueous solution): Only terminal absorption visible
    8) $^1$H-NMR spectrum (500 MHz, in $D_2O$): As shown in FIG. 1 herein
    9) Colour reaction: Positive in the reactions with anisaldehyde, sulfuric acid and iodine; negative in the reactions with ninhydrin, dinitrophenylhydrazine, ferric chloride, bromocresol green and Dragendorff's reagent.

2. A composition antagonistic to ANP receptors comprising an effective amount of a compound of claim 1 in admixture with a physiologically acceptable carrier or excipient.

3. A HS-142-1 compound comprising a linear $\beta 1 \rightarrow 6$ glucan esterified by caproic acid, the number of D-glucose residues being 17 and the number of caproic acid residues being 11, having substantially the following physio-chemical characteristics:
1) Nature: White powder
2) Melting point: 175°–185° C.
3) Molecular formula: $C_{150}H_{252}O_{94}$
4) Mass spectrum (negative mode FAB mass spectrum): Found: M/Z 3557.9 (M-H)$^-$ Calculated: M/Z 3558.5
5) Specific rotation: $[\alpha]^{24}_D = -21.1°$ (c 0.06, aqueous solution)
6) Infrared absorption spectrum (KBr tablet method): cm$^{-1}$: 3425, 2925, 1730, 1645, 1455, 1375, 1250, 1170, 1050
7) Ultraviolet absorption spectrum (aqueous solution): Only terminal absorption visible
8) $^1$H-NMR spectrum (500 MHz, in D$_2$O); as shown in FIG. 2 herein
9) Colour reaction: Positive in the reactions with anisaldehyde, sulfuric acid and iodine; negative in the reactions with ninhydrin, dinitrophenylhydrazine, ferric chloride, bromocresol green and Dragendorff's reagent.

4. A composition antagonistic to ANP receptors comprising an effective amount of a compound of claim 3 in admixture with a physiologically acceptable carrier or excipient.

5. A HS-142-1 compound comprising a linear $\beta 1 \rightarrow 6$ glucan esterified by caproic acid, the number of D-glucose residues being 13 and the number of caproic acid residues being 6, having substantially the following physio-chemical characteristics:
1) Nature: White powder
2) Melting point: 175°–185° C.
3) Molecular formula: $C_{114}H_{192}O_{72}$
4) Mass spectrum (negative mode FAB mass spectrum): Found: M/Z 2713.3 (M-H)$^-$ Calculated: M/Z 2734.1
5) Specific rotation: $[\alpha]^{24}_D = -26.2°$ (c 0.4, aqueous solution)
6) Infrared absorption spectrum (KBr tablet method): cm$^{-1}$: 3400, 2935, 1735, 1650, 1460, 1380, 1255, 1165, 1050
7) Ultraviolet absorption spectrum (aqueous solution): Only terminal absorption visible
8) $^1$H-NMR spectrum (500 MHz, in D$_2$O): As shown in FIG. 3 herein
9) Colour reaction: Positive in the reactions with anisaldehyde, sulfuric acid and iodine; negative in the reactions with ninhydrin, dinitrophenylhydrazine, ferric chloride, bromocresol green and Dragendorff's reagent.

6. A composition antagonistic to ANP receptors comprising an effective amount of a compound of claim 5 in admixture with a physiologically acceptable carrier or excipient.

* * * * *